United States Patent [19]

Norfleet

[11] 4,235,874

[45] Nov. 25, 1980

[54] DENTIFRICE

[75] Inventor: James Norfleet, Plainfield, N.J.

[73] Assignee: Colgate Palmolive Company, New York, N.Y.

[21] Appl. No.: 47,600

[22] Filed: Jun. 11, 1979

[51] Int. Cl.³ .......................... A61K 7/16; A61K 7/18
[52] U.S. Cl. ......................................... 424/52; 424/57
[58] Field of Search .................................. 424/49–58, 424/52, 57

[56] References Cited

U.S. PATENT DOCUMENTS

| | | | |
|---|---|---|---|
| 2,272,617 | 2/1942 | Cox et al. | 424/57 |
| 2,876,168 | 3/1959 | Broge et al. | 424/57 |
| 2,901,400 | 8/1959 | Thomas | 424/57 |
| 3,012,852 | 12/1961 | Nelson | 424/57 |
| 3,112,247 | 11/1963 | Schweizer | 424/57 |
| 3,310,372 | 1/1967 | Wright | 424/57 |
| 3,357,790 | 12/1967 | Saunders et al. | 424/57 |
| 3,450,813 | 6/1969 | Muhler | 424/57 |
| 3,989,814 | 11/1976 | Cordon et al. | 424/57 |
| 4,117,109 | 9/1978 | Stookey | 424/57 |
| 4,170,634 | 10/1979 | Cordon et al. | 424/57 |

*Primary Examiner*—Shep K. Rose
*Attorney, Agent, or Firm*—Robert L. Stone; Murray M. Grill; Herbert S. Sylvester

[57] ABSTRACT

A new and improved dentifrice including a mixture of polishing agents, the combination providing improved polishing without significant increase in abrasion.

13 Claims, No Drawings

DENTIFRICE

This invention relates to a new and improved dentifrice, more particularly, a dentifrice having a unique polishing agent comprising a main or primary polishing agent and a minor amount of a secondary polishing agent.

Conventional dentifrice abrasives have as their most important function, the removal of debris and residual stain from the teeth and the polishing of the tooth surface. Several of the most commonly used abrasives are capable of performing both of these functions.

Abrasivity of dentifrices as measured through radioactive dentin abrasion (RDA) is considered an excellent parameter in determining the cleaning potential of a given dentifrice. The RDA is determined in a procedure based on technique described in the literature; e.g. Stookey et al, "Journal Of Dental Research," Vol. 47, pages 524–538 (1968). Such qualities as particle hardness and average particle diameter (APD) have been shown to directly effect the RDA of abrasive materials. Generally, a RDA range of approximately 350–500 is desirable in that it does not have a deleterious effect on dentin, the soft tissue of the tooth, and is effective since the product is capable of removing debris and residual stain from the tooth surface when used with a toothbrush as routine aids to good oral hygiene. Most commerically available dentifrices fall within this range. Some dentifrice abrasives, however, such as dicalcium phosphate dihydrate (APD 4.2±0.4 microns), hydrated alumina (APD 6.5±8.5 microns) or silica xerogel, such as that available under the trademark Syloid 74 (APD 8 microns), available from Davison Chemical Division, W. R. Grace and Company have inherently low to moderate RDA's (about or even less than 200 to about 300 in about 50% aqueous slurry). The cleaning effectiveness of these materials is enhanced by the use of abrasive adjuncts or secondary polishing agents; materials generally smaller in particle size but significantly harder than conventional abrasives. Anhydrous dicalcium phosphate (ADCP), zirconium silicate or crystalline silica, available under the trademark Minusil from Pennsylvania Glass Sand Corporation have been suggested as such agents.

The present invention employs normal calcium pyrophosphate as a secondary polishing agent. This material has been found to substantially increase the RDA's of low abrasive dentifrice formulations without, however, damaging the tooth surface.

It is accordingly an object of the present invention to provide for an increase in cleaning potential of a given polishing agent by the combination thereof with normal calcium pyrophosphate.

This and other objects of the invention will become more apparent from the following detailed disclosure and claims.

Broadly speaking, the instant invention includes the provision of a dentifrice composition comprising about 19 to 85% of a water insoluble primary polishing agent and about 1 to 10% of normal calcium pyrophosphate as a secondary polishing agent in combination therewith, said normal calcium pyrophosphate having a radioactive dental abrasion value of about 1170 in about 50% aqueous slurry.

Toothpastes contain a dental vehicle which forms a gel or creamy mass of a consistency which can be desirably extruded from a collapsible tube such as aluminum tube or a lead tube. The vehicle contains liquids and solids. In general, the liquid portion comprises water and humectants such as glycerine, sorbitol, propylene glycol, polyethylene glycol 400 or the like including suitable mixtures thereof. It is usually advantageous to use a mixture of both water and humectant, such as glycerine, sorbitol, propylene glycol or the like. The total liquid content is generally about 20–79.5% by weight of the toothpaste, usually about 20–50%.

The solid portion of the vehicle is a gelling agent, such as the natural and synthetic gums and gum-like materials, such as Irish Moss, gum tragacanth, alkali metal carboxymethyl cellulose and hydroxymethyl carboxyethyl cellulose, polyvinyl pyrrolidone, starch, water soluble, hydrophillic colloidal carboxyvinyl polymers, such as those sold under the trademark Carbopol 934 and 940. The solid portion of the vehicle is typically present in an amount up to about 10% by weight of the toothpaste and preferably about 0.5–5% by weight.

These oral compositions normally have a pH between about 5 and 9 and preferably about 6-8. If desired, the pH may be maintained with a buffering system.

In a dentifrice there is present therein as the primary polishing agent a substantially water-insoluble polishing agent of the type commonly employed in dental creams, chewable tablets and powders. There are relatively large numbers of such materials known in the art. Representative materials include for example, insoluble phosphate salts, such as insoluble sodium metaphosphate, insoluble potassium metaphosphate, dental grade calcium pyrophosphate, magnesium orthophosphate, tricalcium phosphate, dicalcium phosphate dihydrate, anhydrous dicalcium phosphate and the like. Other polishing agents include calcium carbonate, magnesium carbonate, hydrated alumina and colloidal silica. Combinations of polishing agents may be employed. The preferred polishing agents are the dicalcium phosphates and insoluble sodium metaphosphate.

The primary and secondary polishing agents may be the sole carrier materials, particularly when the dentifrice is a toothpowder. Typically, other ingredients are present in the carrier and the amount of polishing agents is up to about 95% by weight of the carrier. In the case of a dental cream or chewable tablet the amount of primary and secondary polishing agents is generally about 20–75% by weight and in a toothpowder it is generally about 70–95% by weight.

In chewable dental tablets the solids and liquids are proportioned similarly to the amounts in dental creams. A waxy matrix such as polyethylene glycol having a molecular weight of about 6,000 is also present, generally in amounts of about 4–20% by weight, in order to facilitate forming a tablet of desired size and shape.

In accordance with the instant invention it has been found that as little as about 1 to 10% normal calcium pyrophosphate ($Ca_2P_2O_7$), preferably about 2 to 5%, more preferably about 3 to 5%, is effective in increasing the RDA of the main polishing agent.

Organic surface-active agents may be used in the carrier of the present invention to assist in achieving thorough and complete dispersion of the instant compositions throughout the oral cavity, and render the instant compositions more cosmetically acceptable. The organic surface active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates such as sodium dodecyl benzene sulfonate, higher alkyl sulfoacetates, higher fatty acid ester of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl or N-palmitoyl sarcosinates, which should be substantially free from soap of similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid in the oral cavity due to carbohydrates, in addition to exerting some reduction in the solubility of tooth enamel in acid solutions.

Other suitable surface-active materials include nonionic agents such as condensates of sorbitan monostearate with approximately 60 moles of ethylene oxide, condensates of ethylene oxide with propylene oxide condensates of propylene glycol ("Pluronics") and cationic surface-active germicides and antibacterial compounds such as di-isobutylphenoxyethoxyethyl dimethyl benzyl ammonium chloride, benzyl dimethyl stearyl ammonium chloride, tertiary amines having one fatty alkyl group of from 12 to 18 carbon atoms and two (poly) oxyethylene groups attached to the nitrogen (typically containing a total of from about 2 to 50 ethenoxy groups per molecule) and salts thereof with acids, and compounds of the structure:

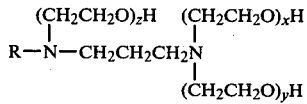

where R is a fatty alkyl group containing from about 12 to 18 carbon atoms, and x, y and z total three or higher, as well as salts thereof with mineral or organic acids.

There may also be employed olefin sulfonate detergents, typically long chain alkenyl sulfonates.

The α-olefin feedstock preferably contains olefins of 8–25 carbon atoms, most preferably 12–21 carbon atoms. The feedstock may contain minor amounts of other constituents, such as secondary or internal olefins, diolefins, cyclic olefins, armomatics, naphthalenes, and alkanes. Best results have been obtained when α-olefins (where $R_1$ is H) constitute a major proportion, for example, about 70% and preferably at least 90% of the feedstock. A particularly preferred olefin feedstock contains in the range of about 12 to 21 carbon atoms in the molecule and yields olefin sulfonates having excellent detergency properties. Especially good foaming characteristics have been obtained by the use of a feed stock whose alpha-olefin content consists essentially of compounds of 15 to 18 carbon atoms.

The detergent material typically contains at least about 50% by weight of long-chain alkenyl sulfonate, up to about 33% by weight of hydroxy alkane sulfonate, and up to about 15% of impurities, such as long-chain water-insoluble sultones, most of which impurities are characterized as being soluble in acetone.

The olefin sulfonate is generally employed in the form of its sodium salt. It is within the scope of the invention to use other water-soluble salts, for example, salts of other alkali metals such as potassium salts of alkaline earth metals, such as magnesium and calcium, triethanolamine, salts and the like, as well as mixtures of a salt such as a sodium salt with the free olefin sulfonic acid.

It is preferred to use the surface active agent in amounts of about 0.05–5% by weight of the carrier.

Various other materials also may be incorporated in the carrier. Examples thereof are coloring or whitening agents, preservatives, silicones, chlorophyll compounds, ammoniated materials such as urea, diammoniumphosphate and mixtures thereof, and other constituents. These adjuvants are incorporated in the instant compositions in amounts which do not substantially adversely affect the properties and characteristics suitably selected and used in proper amount depending upon the particular type of preparation involved.

It may be desirable too to include antibacterial agents in the carrier, typically in amounts of about 0.01–5%, preferably about 0.05–1.0%, by weight of the carrier. Typical antibacterial agents include:

$N^2$-(4-chlorobenzyl)-$N^3$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^3$-p-chlorobenzylbiguanide,
1,6-di-p-chlorophenylbiguanidohexane;
1-(lauryldimethylammonium)-8(p-chlorobenzyldimethylammonium octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydro pyrimidine;
and their nontoxic acid addition salts.

Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2.KF$), sodium hexafluorostannate, stannous chlorofluoride, sodium fluorozirconate and sodium monofluorophosphate. These materials which dissociate or release fluorine-containing ions in water, suitably may be present in an effective but non-toxic amount, usually within the range of about 0.01 to 1% by weight of the water soluble fluorine content thereof.

The normal calcium pyrophosphate employed herein has the formula $Ca_2P_2O_7$, a molecular weight of 254.1, a typical analysis of about 43.7% of CaO, 55.6% $P_2O_5$, 0.15% ignition loss; the mean particle size thereof being about 13.5 microns. At a level of about 50% by weight it has an RDA of about 1170 as compared to an RDA of about 350, 400 for 50% dental grade calcium pyrophosphate, which has been used in dentifrice for instance as described in U.S. Pat. Nos. 2,876,166; 2,876,168; 3,112,247; and 4,117,109.

A toothpaste of the invention is formed by dispersing a gelling agent such as sodium carboxymethyl cellulose or Carbopol 934 and a preservative such as sodium benzoate, if employed, with a humectant such as glycerine. Water may also be present. Additional humectant and water, as a 70% sorbitol solution, may then be mixed with the dispersion and heat is applied at about 40°–60° C., say 50° C., to form a paste, gel or cream. Surface-active agent, such as sodium lauryl sulfate, if employed, is then dispersed in the mixture. The preparation is then deaerated and cooled. Desired flavor may then be added and the paste again deaerated. The toothpaste is then tubed.

The following specific examples are further illustrative of the nature of the present invention, but it is understood that the invention is not limited thereto. The amounts and proportions of compositions described in the examples are by weight unless otherwise specified.

EXAMPLE 1

A dental cream is formulated in the usual manner, having the following composition.

| COMPONENTS | PARTS |
| --- | --- |
| Glycerine | 25.7 |
| Tetrasodium Pyrophosphate | 0.25 |
| Carboxymethyl Cellulose | 0.75 |
| Sodium Benzoate | 0.5 |
| Water | 14.6 |
| Sodium Lauryl Sulfate | 1.0 |
| Sodium N-Lauroyl Sarcosinate | 0.7 |
| Dicalcium Phosphate | 46.7 |
| Normal Calcium Pyrophosphate | 5.0 |

EXAMPLES 2–3

Dental creams are formulated, the compositions being as follows:

| Components | A | B |
| --- | --- | --- |
| Glycerine | 28.5 | 25.1 |
| Irish Moss | 1.3 | 1.3 |
| Tetrasodium Pyrophosphate |  | 0.25 |
| Sodium Benzoate | 0.15 | 0.5 |
| Saccharine |  | 0.2 |
| Sodium Lauryl Sulfate | 1.5 | 1.0 |
| Water | 17.4 | 13.9 |
| Sodium N-Lauroyl Sarcosinate | 2.0 | 2.0 |
| Stannous Fluoride | 0.4 |  |
| Sodium Monofluorophosphate |  | 0.76 |
| Normal Calcium Pyrophosphate | 5.0 | 5.0 |
| Dicalcium Phosphate Dihydrate | 2.0 | 47.0 |
| Hydrated Alumina | 45.0 |  |
| Color | 0.4 |  |

EXAMPLE 4

A chewable dental tablet is formulated as follows:

| Components | Parts |
| --- | --- |
| Dicalcium Phosphate | 76.1 |
| Normal Calcium Pyrophosphate | 3.0 |
| Sodium Lauryl Sulfate | 0.5 |
| Hydrogenated Coconut Oil Monoglyceride |  |
| Sulfate Sodium Salt | 1.2 |
| Di-isobutyl Phenoxyethoxyethyl Dimethylbenzyl Ammonium Chloride | 0.1 |
| Polyethylene Glycol 6000 | 10.0 |
| Starch | 2.5 |
| Carboxymethyl Cellulose | 1.25 |
| Silicon Dioxide | 1.25 |
| Polyvinyl Alcohol | 2.9 |
| Talc | 2.0 |

COMPARATIVE EXAMPLES 5–13

The following examples exhibit the effects of normal calcium pyrophosphate and anhydrous dicalcium on the RDA's of otherwise low abrasive dentifrices.

| % PRIMARY POLISHING AGENT | SECONDARY POLISHING AGENT | RDA |
| --- | --- | --- |
| 5- 52% Dicalcium Phosphate Dihydrate (DCPD) | — | 234 |
| 6- 47% DCPD | 5% ADCP | 350 |
| 7- 47% DCPD | 5% Normal $Ca_2P_2O_7$ | 493 |
| 8- 52% Hydrated Alumina (Alcoa C-333) | — | 300 |
| 9- 50% Hydrated Alumina (Alcoa C-333) | 2% Normal $Ca_2P_2O_7$ | 436 |
| 10- 18% Syloid 74 (Silica Xerogel) | — | about 75 |
| 11- 16% Syloid 74 | 5% Normal $Ca_2P_2O_7$ | about 325 |

The foregoing clearly shows a marked improvement in the polishing power of conventional abrasives when they are employed in conjunction with normal calcium pyrophosphate.

The foregoing is unexpected and surprising in view of the fact that the inclusion of small amounts of other polishing agents does not result in such markedly improved RDA's (example 6).

It is noteworthy that the improvement demonstrated occurs even though the RDA values of ADCP, and normal $Ca_2P_2O_7$ are substantially equal (1057 and 1170) for 50% slurries of each respectively.

Although this invention has been described with reference to specific examples, it will be apparent to one skilled in the art that various modifications may be made thereto which fall within its scope.

I claim:

1. A dentifrice composition having improved polishing power comprising (1) about 19 to 85% of a water-insoluble primary polishing agent selected from the group consisting of insoluble sodium metaphosphate, insoluble potassium metaphosphate, dental grade calcium pyrophosphate, magnesium orthophosphate, tricalcium orthophosphate, dicalcium phosphate dihydrate, anhydrous dicalcium phosphate, calcium carbonate, magnesium carbonate, hydrated alumina, colloidal silica and equivalents thereof having a radioactive dentin abrasion value of less than about 300 and (2) about 1 to 10% of normal calcium pyrophosphate having a radioactive dentin abrasion value of about 1170 in about 50% aqueous slurry.

2. The dentifrice composition of claim 1 wherein about 2 to 5% of normal calcium pyrophosphate is present.

3. The dentifrice composition claimed in claim 1 wherein said water insoluble primary polishing agent has a radioactive dental abrasion value of less than about 300 in about 50% aqueous slurry.

4. The composition of claim 3 wherein said water insoluble primary polishing agent is selected from the group consisting of dicalcium phosphate-dihydrate, hydrated alumina, silica xerogel and calcium carbonate.

5. The composition as defined in claim 1 and a carrier for said polishing agents.

6. The composition of claim 5 wherein said carrier comprises water, humectant and gelling agent is an aqueous vehicle.

7. The composition of claim 5 wherein said carrier includes a dentally beneficial fluorine containing compound, which fluorine-containing compound is present in an amount necessary to provide 0.01–1% by weight of the carrier of water-soluble fluorine.

8. The composition of claim 6 wherein said fluorine-containing compound is selected from the group consisting of stannous fluoride and sodium monofluorophosphate.

9. The toothpaste as defined in claim 6 wherein said dental vehicle contains as humectant sorbitol and as gelling agent sodium carboxymethyl cellulose.

10. The toothpaste as defined in claim 4 wherein said water-insoluble primary polishing agent is dicalcium phosphate dihydrate.

11. The toothpaste as defined in claim 4 wherein said water-insoluble primary dental polishing agent is calcium carbonate.

12. The toothpaste as defined in claim 4 wherein said water-insoluble primary dental polishing agent is hydrated alumina.

13. The toothpaste as defined in claim 4 wherein said water-insoluble primary dental polishing agent is silica xerogel.

* * * * *